United States Patent [19]

Satyapal et al.

[11] Patent Number: 5,689,008

[45] Date of Patent: Nov. 18, 1997

[54] CATALYTIC REACTION RATE ENHANCEMENT AT LOW TEMPERATURES

[75] Inventors: Sunita Satyapal, Vernon; Arthur S. Kesten, West Hartford; Joseph J. Sangiovanni, West Suffield; James Freihaut, South Windsor; Charles C. Evans, Vernon, all of Conn.

[73] Assignee: United Technologies Corporation, Hartford, Conn.

[21] Appl. No.: 595,536

[22] Filed: Feb. 2, 1996

[51] Int. Cl.$^6$ .................................................. C07C 29/141
[52] U.S. Cl. ........................ 568/403; 568/402; 502/326; 204/157.62; 204/157.42
[58] Field of Search .................................. 568/403, 402; 502/326; 204/157.62, 157.42

[56] References Cited

U.S. PATENT DOCUMENTS 5,387,397  2/1995  Faux et al. ............................ 422/129

OTHER PUBLICATIONS

Saito et al;Bull.Chem.Soc.Jpn.;61,pp. 961–965, 1988.
House et al;Modern Synthetic Reactions;Second Edition; pp. 34–36, 1972.
The Chemical Society of Japan, Mar. 1988, pp. 961–965, Michio Noda et al., "Liquid–Phase Dehydrogenation of 2–Propanol by Suspended Nickel Fine–Particle Catalyst".
Paper No. 203, pp. 1167–1174, entitled "La cinetique quantitative en catalyse heterogene. La deshydrogenation des alcools secondaires sur le nickel" by Francois Claes et Joseph C. Jungers; (1957).
Mechanical Engineering, Sep. 1994, pp. 82–85, R.S. Wegeng and M.K. Drost, "Developing new miniature energy systems".
Proceed.8th World Hydrogen Energy Conference, vol. 1, pp. 339–344, 1990, Y. Saito et al., "Hydrogen Production From 2–Propanol As A Key Reaction For Chemical Heat Pump With Reaction Couple Of 2–Propanol Dehydrogenation/ Acetone Hydrogenation".

*Primary Examiner*—C. Warren Ivy
*Assistant Examiner*—Sreeni Padmanabhan
*Attorney, Agent, or Firm*—Pamela J. Curbelo

[57] ABSTRACT

The present invention relates to sustaining high reaction rates at lower reaction temperatures than conventionally utilized with the particular catalyst. The improved reaction rates are obtained using various techniques and combinations thereof including simulated boiling, utilizing the reactant in the form of a thin film, employing microwaves, and the use of micromachines.

17 Claims, 1 Drawing Sheet

CATALYTIC REACTION RATE ENHANCEMENT AT LOW TEMPERATURES

TECHNICAL FIELD

The present invention relates to the enhancement of catalytic reaction rates at low temperatures, and particularly relates to utilizing microwaves, simulated boiling, ultrasonication, thin films and combinations thereof to enhance catalytic reaction rates at temperatures lower than conventionally employed.

BACKGROUND OF THE INVENTION

Many reactions require a minimal degree of heat to proceed. Often, however, additional heat is required to enhance reaction rates to improve efficiency and to inhibit catalyst poisoning. Liquid reactant catalytic reactions were often run at the reactant's boiling point to increase the reaction rates, facilitate vaporization of the reaction products and prevent adsorption of the reaction products on the catalyst surface. In some instances, solvents were added to the reactant to raise the reactant's boiling point, thereby allowing the reaction to be conducted at an even higher temperature to further inhibit catalyst poisoning and to improve the reaction kinetics. (As used herein "the reactant's boiling point" means the boiling point of the reactant itself or the reactant solution, whichever is higher.)

One example of a conventional process which typically operates at the reactant's boiling point is the liquid phase dehydrogenation of isopropanol with a powdered catalyst. This process comprises dispersing the powdered catalyst in the isopropanol and heating the dispersion to temperatures of at least the boiling point of isopropanol (about 82° C.). Reaction rates obtained with this process typically ranged from a hydrogen evolution rate of about 390 mmol/hr-g up to 4630 mmol/hr-g depending upon the catalyst employed. (Y. Saito et al., Proc. 8th World Hydrogen Energy Convention, Vol. 1,339 (1990)) Conducting the reaction at this high temperature provides high intrinsic kinetic rates and reduces catalyst degradation by facilitating the removal of the reaction products, acetone and hydrogen, from the catalyst via desorption and from the isopropanol via vaporization. Temperatures below about 82° C., however, result in reduced reaction kinetics and in reduced catalyst life due to the poisoning of the catalyst via the adsorption of acetone, while increased reaction temperatures often result in an increase in side reactions, unwanted by products, and increased operation costs.

With conventional methods of providing heat for chemical reactions (e.g., flame, resistive heater, hot plate, hot oil, furnace, etc.) heat is generated externally to the object to be heated. This heat is then transferred via conduction and/or convection to the object with the surface of the object heated first. Only after the surface is heated does the heat flow to the interior of the object. Consequently, the interior always remains cooler than the surface. Thus in a conventional slurry bulk reactor used for the dehydrogenation of isopropanol, as shown in FIG. 1, the temperature of the catalyst surface can never be higher than the temperature of the surrounding isopropanol liquid. Therefore, there is a balance between the high kinetic rates achieved with high temperatures and the high isopropanol vaporization caused by those temperatures. Optimally, a system should employ high catalyst surface temperatures to enhance the kinetics, while keeping the bulk isopropanol at low temperatures to reduce vaporization thereof.

What is needed in the art is a method for sustaining catalytic reaction rates at lower temperatures.

DISCLOSURE OF THE INVENTION

The present invention relates to methods for improving the catalytic reaction rate of a liquid reactant. One method comprises the steps of: contacting the reactant and a catalyst; providing heat at a temperature below the boiling point of the reactant to catalytically activate the catalyst; reacting the reactant to form at least one product; and simulating boiling in the reactant to release the product into the gas phase.

Another method comprises: dispersing a thermally conductive catalyst in a liquid reactant having an average bulk temperature, irradiating said dispersion with microwaves to heat said catalyst while substantially maintaining the reactant average bulk temperature; and catalytically reacting the reactant to produce a product.

The foregoing and other features and advantages of the present invention will become clear from the following description and drawings.

BEST MODE FOR CARRYING OUT THE INVENTION

Figure 3:
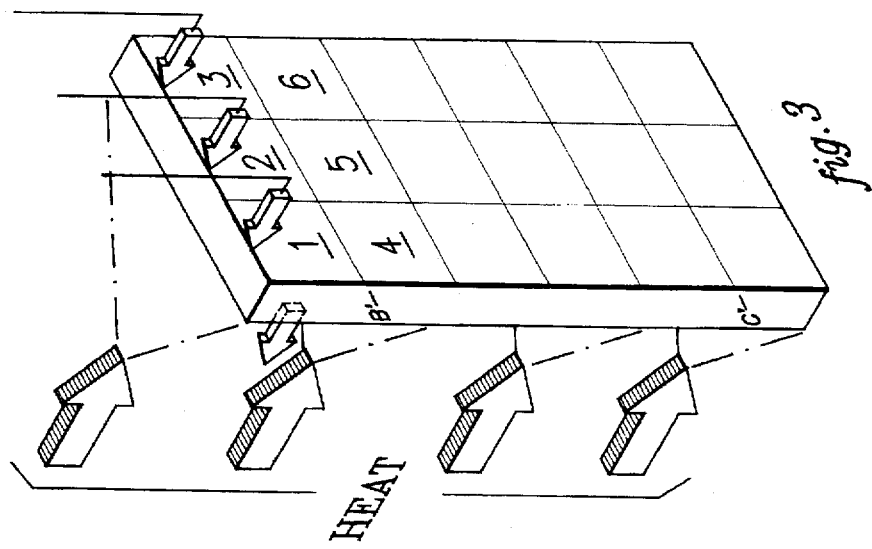
FIG. 3 is a schematic of multiple microreactors forming a unit wherein fresh reactant is received by each reactor.

The present invention will be described in relation to reducing the reaction temperature from the conventional reaction temperature (i.e. the boiling point in most cases) using the dehydrogenation of isopropanol as an example. The present invention, however, is useful in numerous other catalytic reactions which can benefit from the reduction of the reaction temperatures.

Improving the mass transfer of the reaction products through the liquid phase inhibits catalyst poisoning and allows a reduction of the reaction temperature while maintaining conventional reaction rates. Facilitating movement of reaction products to the liquid-gas interface prevents absorption thereof onto the catalyst and assists in the vaporization of those reaction products. Improvement of the mass transfer can be achieved with a simulated boiling technique such as cavitation via bubbling or sparging, ultrasonication, by combinations thereof, or by similar methods. For example, the conventional dehydrogenation of isopropanol requires that the isopropanol be heated to its boiling point (temperatures of about 82° C.) to sufficiently release the reaction products, acetone and hydrogen, from the liquid and to prevent catalyst poisoning. With the present method, however, temperatures of about 74° C. or lower, can be employed in the dehydrogenation of isopropanol without a greater degree of catalyst poisoning than was present at 82° C. Simulated boiling can allow a temperature reduction of greater than about 7° C. and often up to and exceeding about 12° C. from the conventional reaction temperature (in this instance, the reactant's boiling point), without increasing the degree of catalyst poisoning. Additionally, the observed reaction rate is higher than conventional reaction rates obtained at the same temperature, and theoretically, these reaction rates are substantially equivalent to the prior art reaction rates obtained at the conventional temperatures.

The reaction temperature can be further reduced by, in addition to simulated boiling, also employing ultrasonication during the reaction process to facilitate movement of both the reaction products and the bubbles to the liquid-gas interface. In such an instance, the temperature reduction should be in the order of about 10° C. and possibly to greater than about 17° C. of the conventional reaction temperature while maintaining the reaction rates.

For example, the conventional reaction temperature for the dehydrogenation of isopropanol is about 82° C. According to a theoretical model, "natural boiling" (estimated at a moderate boiling rate of about 0.0015 $gN_2/cm^2$ sec. to about 0.00001 $gN_2/cm^2$ sec.) at 82° C. establishes a hydrogen evolution rate of about 2500 mmol/m²hr (all measurements are at 100 seconds after initiating the dehydrogenation). Since natural boiling is predicted to be a somewhat stronger rate, about 3500 mmol/m²hr is anticipated. In comparison, with intense simulated boiling at a rate of 0.001 $gN_2/cm^2$ sec. to about 0.0015 $gN_2/cm^2$ sec. and a temperature of 72° C., the hydrogen evolution rate is also calculated to be about 3500 mmol/m² hr. Consequently, with the use of simulated boiling, the reaction temperature can be reduced from about 82° C. to about 72° C. while maintaining the reaction rates, or at minimum, significantly improving the reaction rate at the lower temperature. It has been confirmed that simulated boiling substantially improves the reaction rate, i.e. by a factor of about 1.5, as compared to operating at the same temperature without simulated boiling. (see Example 3)

Simulated boiling can be accomplished by employing those gases which will not react with the particular catalyst and reactant in which the boiling is simulated. These gases include, but are not limited to, the inert gases (helium, neon, argon, xenon, krypton), mixtures thereof, and other non-reactive gases including, but not limited to, nitrogen.

Another embodiment of the present invention based upon mass transfer characteristics employs a thin film of reactant, i.e. up to about 1.0 millimeters thick, with about 0.05 mm to 0.3 mm preferred, over a solid catalyst. This method reduces the mass transfer requirements of the system by decreasing the diffusion length of the reaction products through the liquid reactant. As with the simulated boiling, the thin film allows the reduction of the reaction temperature without adversely effecting the reaction rate. An additional benefit of this method is that the flow of the thin film reactant can be pulsed on and off to further improve the reaction rates by regenerating or otherwise refreshing the reactant and/or regenerating the catalyst during the periods of ceased reactant flow.

As with mass transfer characteristics, adjustment in the heating characteristics of the system can further improve reaction rates and/or decrease the reaction temperature. Employing a thermally conductive catalyst and heating that catalyst with microwaves allows the reaction to occur at high temperatures while maintaining a relatively low average liquid bulk temperature. Additionally, by heating the catalyst and not the dispersion (catalyst and reactant), the catalyst can be regenerated, in situ, thereby promoting the removal of adsorbed reaction products, while allowing the overall reaction to occur at high reaction rates and lower average bulk temperatures.

Upon contacting the thermally conductive catalyst, the microwaves heat the catalyst to provide pad or all of the necessary heat of reaction to induce the catalytic reaction without heating the entire system. For example, for the dehydrogenation of isopropanol, a platinum-ruthenium (5 wt %) catalyst can be formed on an activated carbon support and dispersed in the isopropanol. (If the catalyst itself does not couple well with microwaves, a suitable support may be used.) The catalyst is then irradiated with microwaves for preferably a sufficient period of time to heat and regenerate the catalyst while sufficiently shod period of time to prevent the vaporization of the isopropanol. Typically, for about 200 ml of isopropanol a period of up to about 150 seconds can be utilized depending is not operating.

Microwaves provide localized heating of the catalyst, thereby kinetically increasing the reaction rates in addition to promoting desorption of reaction products. The microwaves couple with the catalyst surface more efficiently than the liquid reactant, thereby producing a high temperature at the catalyst surface while maintaining a lower bulk liquid temperature. Consequently, the intrinsic rate of reaction will be high at the catalytic site and the desorption of reaction products will be enhanced.

Employing the microwaves in an intermittent, pulsed on and off fashion, further controls the reaction and prevents both over-heating of the liquid reactant or vaporization thereof. Consequently in an intermittent pulsed scenario, the high temperatures at the catalyst reaction sites increase the rate of reaction, facilitate the desorption of the reaction products from the catalyst, and minimize the energy utilization, while substantially maintaining the overall bulk temperature in a more controlled fashion. In other words, by using a pulsed microwave, overall temperatures may be substantially maintained while achieving high reaction rates.

The pulse can be set at regular intervals, i.e. heat with microwaves every 5 minutes for a period of 5 seconds and/or can be based upon the catalyst reactivity. If based upon the catalyst reactivity, when the catalyst reactivity decreases below a predetermined point, the catalyst will be heated with the microwaves for a period sufficient to regenerate the catalyst with minimal vaporization of the reactant. For example, since 200 ml of isopropanol in a 500 ml flask placed in the center of an approximately 0.9 cubic foot, 800 watt (commercial cooking) microwave oven reaches a temperature of about 88° C. in approximately 105 seconds. Consequently, the irradiating period should be less that about 100 seconds under such conditions. Note: the specific time period can vary drastically depending upon the specific microwave oven, the reaction flask location within the oven, and catalyst employed.

The catalytic activity of the catalyst can be further enhanced at lower temperatures by utilizing combinations of the above described methods. For example, the microwaves can be combined with the simulated boiling, ultrasonication, and/or the thin films. The simulated boiling technique can also be utilized with the thin films. Finally, a boiling point reducing substance or azeotrope can be added to the reactant in combination with any of the above techniques; i.e. hexane can be mixed with isopropanol to reduce the boiling point to about 72° C. or lower. When combined techniques are employed, the reaction temperature should be reduced to about 65° C. or lower without increasing the degree of catalyst poisoning conventionally observed, and while significantly improving the reaction rates conventionally obtained at 65° C.

Figure 2:
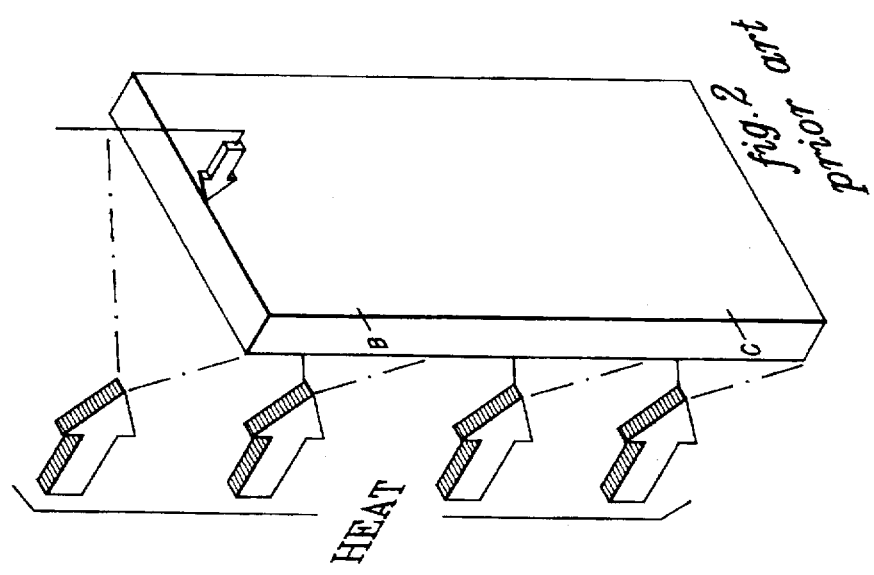
FIG. 2 is a schematic of a thin film bulk reactor.
Figure 1:
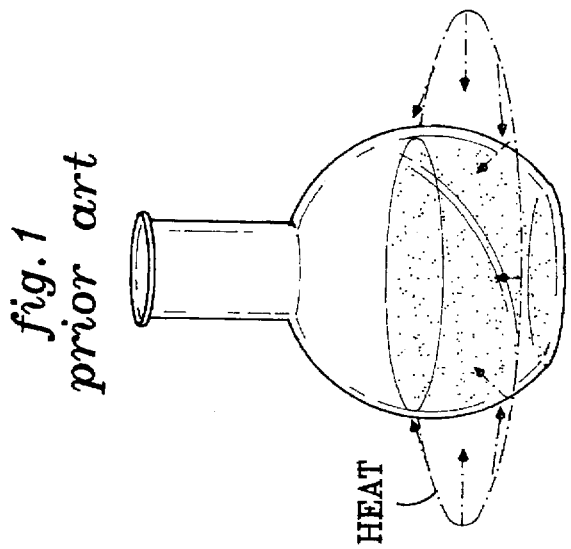
FIG. 1 is a schematic of a conventional slurry bulk reactor.

Finally, the implementation of the present invention can be improved via the use of micromachines. The micromachine system increases the surface area for heat absorption, increases the surface to volume ratio (heat transfer and mass transfer), and permits convenient batchwise operation which allows periodic refreshing of the catalyst. Referring to FIGS. 2 and 3, which is meant to be exemplary not limiting, fresh liquid reactant is introduced to each micromachine, 1, 2 . . . , instead of being introduced to a single large reactor as in FIG. 2. Consequently, unlike the catalyst at points B+C in FIG. 2, the catalyst at the points B' and C' in FIG. 3 will be exposed to fresh isopropanol. Therefore, catalyst degradation due to an increase in acetone will be limited, thereby making the system more efficient. In FIG. 2, although the catalyst at point B will be exposed to relatively fresh reactant, the catalyst at point C will contact reactant substantially diluted with reaction products.

In a thin film bulk system, as is shown in FIG. 2, the reactant flows over the entire catalyst having a surface area (1 unit by 2 units, for example). Although the reactant near the end of the reactor is not completely reacted, the catalyst is not employed to its fullest capacity due to the amount of reaction products in the reactant stream at that point. If the reactors are in the form of a micromachine, the area/reactor over which the reactant must flow is reduced and the overall surface to volume ratio of the system, vs. a prior art system, is increased. In the microreactor the surface area per reactor is significantly reduced (i.e., 1/3rd unit by 1/6th unit). In the microreactor system each reactor receives fresh reactant. Consequently, at 1/6th of the way through the reactor system, point B', fresh reactant is introduced, while in the conventional system, the reactant at point B contains reaction products which can poison the catalyst.

The following examples are meant to further illustrate the present invention and not to limit the scope thereof.

EXAMPLE 1

The dehydrogenation of isopropanol was accomplished at a temperature of about 72° C. via simulated boiling.
1. A dispersion of 200 ml of isopropanol and 200 mg of platinum-ruthenium (5 weight percent on activated carbon) was formed.
2. The dispersion was heated using a hot water bath to a temperature of 72° C.
3. Meanwhile, nitrogen was bubbled through the dispersion at a rate of 11 milliliters per minute to simulate boiling.

Due to the degree of hydrogen evolution observed in the above example, it was determined that the production of acetone and the degree of catalyst poisoning was comparable to that observed in the conventional prior art dehydrogenation of isopropanol at 82° C.

EXAMPLE 2

The following example can be used in the dehydrogenation of isopropanol to reduce the reaction temperature to below about 70° C. while maintaining the reaction rates conventionally obtained at 82° C.
1. A dispersion of 200 ml of isopropanol and 200 mg of platinum-ruthenium (5 weight percent on activated carbon) should be formed.
2. The dispersion should then be heated using microwaves to an average temperature of about 65° C.
3. While the dispersion is heating, nitrogen can be bubbled through the dispersion at a rate of about 1–5 ml/sec. to simulate boiling.
4. When the reaction rate decreases to about 70% of original reaction rate the catalyst can be heated for about 50 sec. with microwaves to regenerate the catalyst.

EXAMPLE 3

Part A

An experiment was conducted using a tube type catalyst (20 cm in length, consisting of Pt (approximately 5 g/m$^2$) on alumina on the inner surface of the tube. The tube was filled with liquid isopropanol and the outside of the tube was heated with heating tape to a tube temperature of 101° C. (isopropanol temperature of 82.4° C.). The acetone evolution rate was measured to be 955 (±190) mmol/hr m$^2$.

Part B

A second experiment was conducted utilizing the identical apparatus filled with liquid isopropanol and the outside of the tube was heated with heating tape to a tube temperature of 79° C. (isopropanol temperature of 74° C.). There was no measurable rate of hydrogen evolution. However, when boiling was simulated via bubbling nitrogen through a perforated tube at a rate of approximately 40 ml/min., the acetone evolution rate was measured to be 362 (±103) mmol/hr m$^2$.

Using an Arrhenius expression with a reported activation energy of 17 kcal/mol to calculate the expected rate at 79° C., the result is 246 mmol/hr m$^2$ (J. C. Jungers, F. Claes, Mem. Soc. Chim., 5° serie, N °203, 1167 (1958); M. Noda, S. Shioda, Y. Saito, Bull. Chem. Soc. Jpn., 61,961 (1988); H. Kameyama, P. Gastauer, University of Tokyo Agriculture and Technology, Tokyo, Japan, experimental results). The observed rate of 362 mmol/hr m$^2$ constitutes a greater than a 1.47 improvement over the conventional rate of 246 mmol/hr m$^2$.

Conventionally reaction rates were increased by increasing the reaction temperature. In order to then reduce the boiling point, a third component was often added to the reactant/catalyst mixture. Both of these techniques, however, supported an increase in unwanted by-products. Note, however, it is understood and anticipated hereby that a temperature reducing substance, such as an azeotrope, can be added to the reactant, in combination with the systems of the present invention to further reduce the reaction temperature. Unlike the prior art, the present invention is capable of improving the reaction rate at lower than conventional temperatures without causing significant catalyst poisoning.

We claim:

1. A method for catalytically reacting a liquid isopropanol reactant, said reactant having a boiling point and a boiling point reaction rate, comprising the steps of:

a. contacting the reactant and a catalyst;
   b. providing heat to catalytically activate the catalyst at a first temperature below the boiling point of the reactant;
   c. reacting the reactant to form at least one product; and
   d. simulating boiling in the reactant;

whereby the reactant reacts at a reaction rate which is substantially equivalent to the boiling point reaction rate of said reactant.

2. A method as in claim 1 wherein said simulated boiling is accomplished by bubbling, sparging, ultrasonication, or combinations thereof.

3. A method as in claim 1 wherein the reactant temperature does not exceed 75° C.

4. A method as in claim 1 wherein said reactant and catalyst are irradiated with microwaves.

5. A method as in claim 1 wherein the reactant is in the form of a film which flows over the catalyst.

6. A method as in claim 1 further comprising the step of mixing an azeotrope with the reactant to form a mixture having a boiling point below the boiling point of the reactant, and wherein said first temperature does not exceed 70° C.

7. A method for catalytically reacting a liquid isopropanol reactant, comprising the steps of:

a. dispersing a thermally conductive catalyst in the liquid reactant, wherein said liquid reactant has an average bulk temperature;

b. irradiating said dispersion with microwaves to heat said catalyst while substantially maintaining the average bulk temperature; and c. catalytically reacting said reactant to produce a product.

8. A method as in claim 7 wherein said liquid reactant is catalytically dehydrogenated to produce acetone and hydrogen.

9. A method as in claim 8 wherein said average bulk temperature does not exceed about 79° C.

10. A method as in claim 8 wherein said average bulk temperature does not exceed about 75° C.

11. A method as in claim 8 wherein said average bulk temperature does not exceed about 65° C.

12. A method as in claim 7, wherein said reactant is isopropanol and said catalyst is platinum-ruthenium on activated carbon and wherein said catalyst is dispersed in said isopropanol.

13. A method as in claim 8 further comprising the step of simulating boiling within the dispersion.

14. A method as in claim 13 wherein said average bulk temperature does not exceed about 60° C.

15. A method as in claim 7 wherein the catalyst is a solid catalyst and the reactant is flowed over the catalyst in the form of a film.

16. A method as in claim 15 wherein said reactant is pulsed over said catalyst.

17. A method as in claim 7 wherein said dispersion is intermittently irradiated with microwaves.

* * * * *